United States Patent [19]

Miller

[11] Patent Number: 6,024,710
[45] Date of Patent: Feb. 15, 2000

[54] BLOOD COLLECTION TUBE CLOSURE FOR USE WITH A NEEDLE HOLDER

[75] Inventor: Henry F. Miller, Clifton, N.J.

[73] Assignee: Becton Dickinson and Company, Franklin Lakes, N.J.

[21] Appl. No.: 09/164,539

[22] Filed: Sep. 30, 1998

Related U.S. Application Data

[60] Provisional application No. 60/045,159, Apr. 30, 1997.

[51] Int. Cl.$^7$ .......................................... A61B 5/00
[52] U.S. Cl. ........................ 600/578; 604/110; 604/195; 604/220
[58] Field of Search ...................................... 600/573, 575, 600/578; 604/110, 195, 187, 192, 197, 198, 220, 225, 226, 263

[56] References Cited

U.S. PATENT DOCUMENTS

| | | |
|---|---|---|
| 4,079,729 | 3/1978 | Cornell . |
| 5,423,758 | 6/1995 | Shaw ........................................... 604/95 |
| 5,632,395 | 5/1997 | Burns ........................................ 215/247 |

*Primary Examiner*—Cary O'Connor
*Assistant Examiner*—Pamela L. Wingood
*Attorney, Agent, or Firm*—Nanette S. Thomas, Esq.

[57] ABSTRACT

An assembly for the collection of a patient's blood specimen comprises an elongate needle holder, a blood collection tube, and a cap closing the blood collection tube. The needle holder supports a blood extracting needle through a closed end thereof. The blood collection tube is insertable into the interior of the needle holder so as to collect blood. The cap has a membrane which is puncturable by the needle upon insertion of the blood collection tube into the interior of the needle holder. The cap includes a deflectable member extending therefrom for engagement with the cylindrical wall of the needle holder so as to frictionally resist longitudinal movement of the tube within the tube holder.

1 Claim, 5 Drawing Sheets

BLOOD COLLECTION TUBE CLOSURE FOR USE WITH A NEEDLE HOLDER

This application claims benefit of Provisional Application No. 60/045,159 filed Apr. 30, 1997.

BACKGROUND OF THE INVENTION

1. Field of the Invention

The present invention relates to an assembly for collecting medical specimens and more specifically, the present invention relates to a cap for a blood collection tube.

2. Description of Related Art

Blood samples and other medical specimens are routinely taken and collected in a specimen collection container. In blood collection applications, the collection container is typically a hollow blood collection tube with one end closed by a semi-spherical portion and the other end open. The open end is sealable by an impervious elastomeric cover. The tube thus defines an interior chamber for collecting and holding the blood sample.

To collect a blood sample, the tube is used in concert with a tube holding device. This device typically comprises a hollow needle extending through the closed end of a tubular housing. The tubular housing has an opposed open end for accepting the blood collection tube. The hollow needle is inserted through the dermal layer into the lumen of the blood vessel and taps into the circulation system of a subject to direct blood therethrough towards the interior compartment of the holding device. The collection container is inserted through the open end of the holder so that the hollow needle punctures through the cover of the collection container. The interior of the collection container is now in direct communication with the circulation system and, having typically been formed in a vacuum, draws blood through the hollow needle and into the collection container. Once the phlebotomist has drawn enough blood into the collection container, the container may be removed from the holder. The container cover, being of an elastomeric material, reseals the hole made by the needle. The phlebotomist may then, if desired, insert a new collection container into the holder to draw more blood.

Some holding devices include a deformable sheath over that portion of the hollow needle extending into the interior of the tubular housing. The sheath covers the entire portion of the needle inside the tubular housing when no blood collection tube is present. When the blood collection tube is longitudinally inserted into the holder, the elastomeric cover of the tube allows the hollow needle to pass therethrough but pushes the sheath back into a compressed position. When the tube is removed from the housing the sheath expands back to cover the hollow needle so that the phlebotomist is not exposed thereto. This spring-like expansion characteristic of the deformable sheath also exerts a force against the cover of the tube, and thereby acts to push the tube out from the housing.

Since the blood collection tube must be maintained in a fixed position within the housing during sample collection, the spring force of the sheath against the tube cover must be overcome.

It is therefore desirable to provide a blood collection tube with improved engagement characteristics for maintaining engagement between the tube and the holding device during sample collection.

SUMMARY OF THE INVENTION

The present invention is an improved assembly for collecting medical specimens. Preferably, the present invention comprises a blood collection tube which is frictionally retained within a tube holding device during the blood collection procedure.

Preferably, the present invention comprises a closure assembly for a medical specimen collection tube. The closure assembly includes a cap placed over the open end of the collection tube. The cap includes an elastomeric membrane which is punctured by the blood expelling end of the needle of a holding device. The cap also includes a deflectable member extending radially from the open end of the collection tube for engaging the interior wall of the holding device. The deflectable member provides improved frictional resistance to any longitudinal movement of the collection tube.

Most preferably, the present invention comprises a closure cap for a cylindrical blood collection tube wherein the cap includes an elastomeric membrane and a deflectable radial member. The deflectable radial member includes an annular skirt having an outwardly flared extent. The annular skirt engages the interior surface of a holding device when a tube having a cap of the present invention is inserted therein. The annular skirt thus prevents unintentional longitudinal movement of the collection tube within the holding device.

The interior of the holding device includes the blood expelling end of a hollow needle which punctures the elastomeric membrane on the tube. The hollow needle further extends through the closed end of the holding device to a blood extracting end which punctures the wall of a subject blood vessel, thereby providing the interior of the collection tube to be in communication with the circulatory system of the subject. The interior of the collection tube, having been formed with a vacuum, draws blood from the blood vessel through the needle.

While the tube is drawing the blood sample, the annular skirt is frictionally engaging the interior of the holding device. The annular skirt deflects inwardly towards the collection tube so that the deflection forces prevent the unintentional longitudinal movement of the collection tube.

DETAILED DESCRIPTION

The present invention is preferably a medical specimen collection container including an improved closure. Most preferably, the closure is a cap for a blood collection tube.

Figure 1:
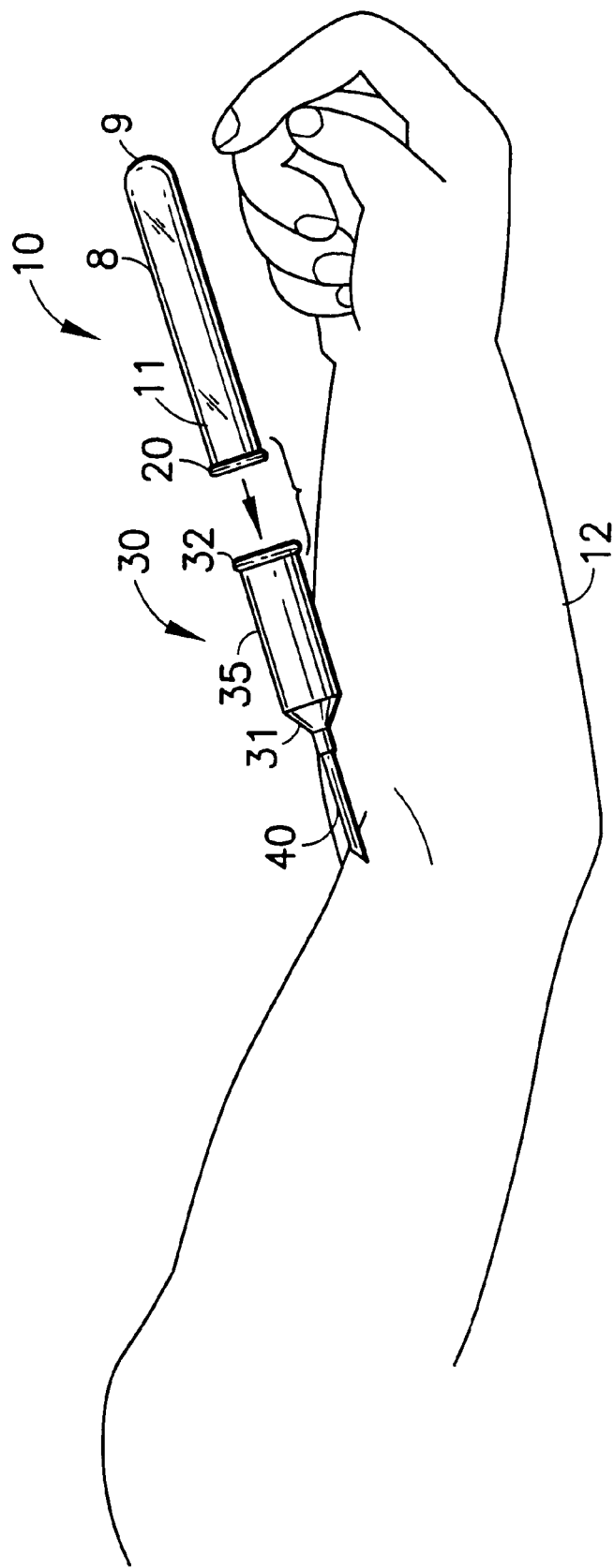
FIG. 1 is a perspective view showing a typical blood sample collection procedure where a blood collection tube and a holding device are use to draw the blood sample from a patient's arm.
Figure 2:
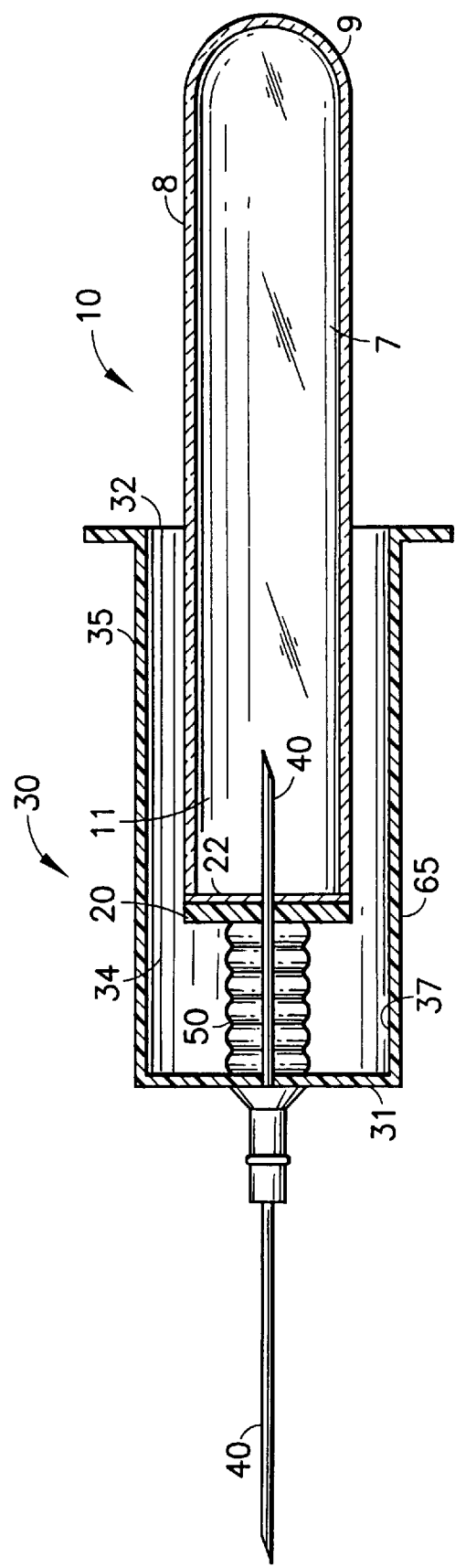
FIG. 2 shows a cross-sectional view of a combination of a blood collection tube and a holding device having a needle with a protective sheath thereover.

Referring to FIGS. 1 and 2, in a typical blood collection procedure, a blood collection tube 10 is used to collect a blood sample from the circulatory system of a patient 12. The blood collection tube 10 is typically a hollow cylindrical tube 8 having one end closed by a semi-spherical closure 9 and an opposed open end 11. The open end 11 is covered with an elastomeric membrane 20. Blood collection tube 10 therefore includes an interior chamber 7 in which to collect blood samples.

A needle holder in the form of a holding device 30 includes a holding tube 35, having a closed end 31 and an opposed open end 32, and a needle holder interior in the form of interior expanse 34 of holding tube 35. Holding device 30 further includes a hollow needle 40 extending through closed end 31 into interior expanse 34 of holding tube 35. Needle 40 includes a blood extracting end exterior of holding tube 35 and a blood expelling end within the interior expanse 34 of holding tube 35. The blood extracting end of needle 40 is percutaneously inserted into the blood stream of a patient 12.

As shown in FIGS. 1 and 2, the covered end of blood collection tube 10 is then inserted into interior expanse 34 of holding tube 35 so that the blood extracting end of needle 40 punctures through elastomeric membrane 20, thereby placing interior chamber 7 of blood collection tube 10 in communication with the blood stream of patient 12. The interior chamber of blood collection tube 10 is typically formed with a vacuum such that, when taking a blood sample, blood is drawn through needle 40 into blood collection tube 10.

As shown in FIG. 2, elastomeric membrane 20 may include a gas barrier 22 spanning the open end of tube 10. The gas barrier is typically formed of a thin metallic foil such as 0.005"-thick aluminum. The membrane 20 allows a needle to pass therethrough while the elastomeric characteristic of the cover tends to reseal the needle puncture when the needle is withdrawn. Membrane 20 is not limited to the flat disk-shape shown in FIGS. 2–5. Other configurations of membrane 20 may also be employed.

As also shown in FIG. 2, holding device 30 typically includes a protective elastomeric sheath 50 which covers the blood expelling end of needle 40 within the interior expanse 34 of holding tube 35. When blood collection tube 10 is inserted into holding device 30, needle 40 punctures through the tip of elastomeric sheath 50 and then through membrane 20. Sheath 50, unable to also penetrate membrane 20, therefore compresses against the interior surface of closed end 31. FIG. 2 shows sheath 50 in the contracted position assumed when blood collection tube 10 is inserted into holding device 30. Note in FIG. 2 that needle 40 is penetrating through membrane 20 while sheath 50 is compressed towards the interior surface of end 31. When blood collection tube 10 is withdrawn from holding device 30, sheath 50 will elastically expand back, in a spring-like manner, to its original position, covering the blood expelling end of needle 40.

Thus while sheath 50 is compressed, its spring-like characteristic exerts a force against membrane 20 in a manner similar to a compressed spring. The spring force that compressed sheath 50 exerts against membrane 20 tends to push blood collection tube 10 off of needle 40. The present invention addresses this tendency of the compressed sheath 50 to push against blood collection tube 10 with a technique for maintaining a frictional retaining force against the interior wall 37 of holding device 30.

Figure 3:
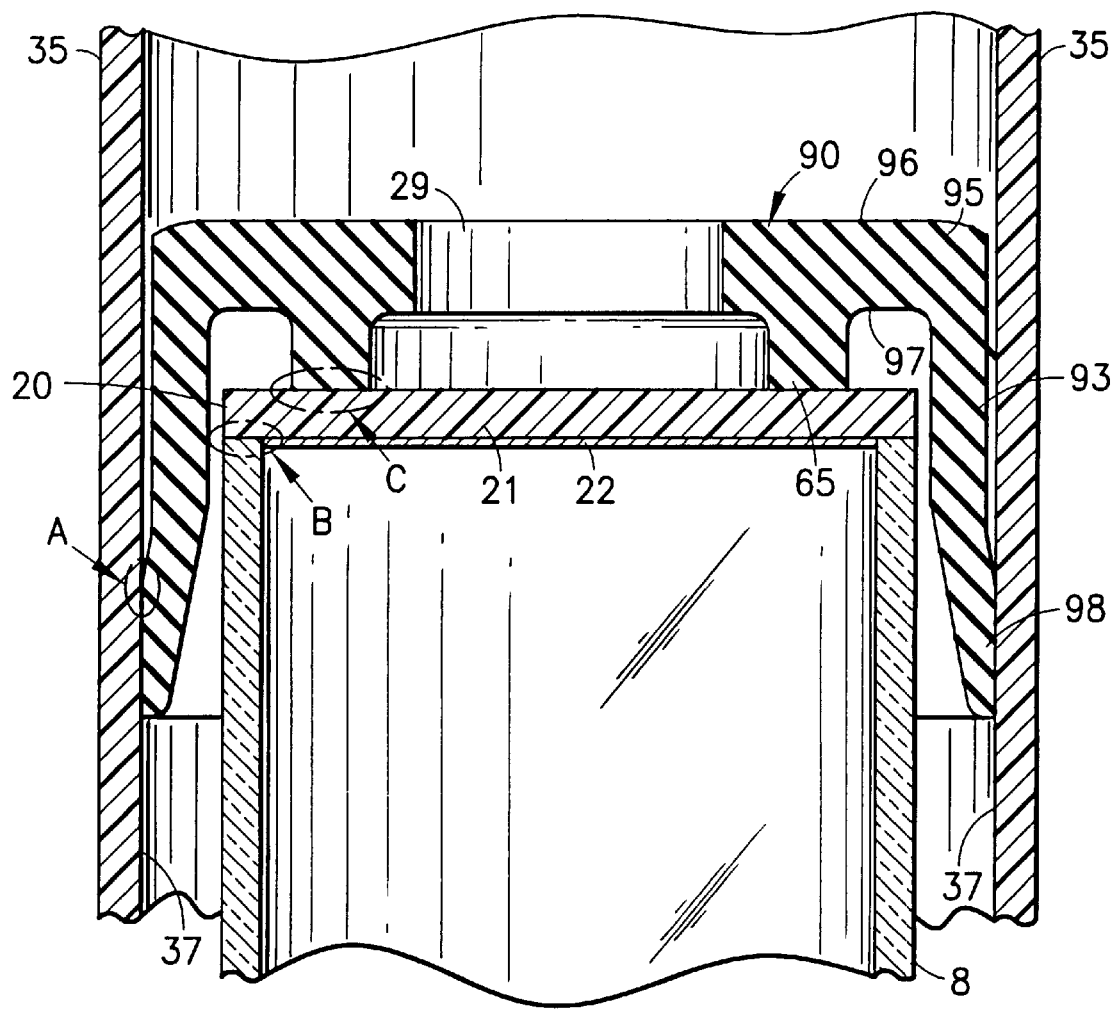
FIG. 3 is a side view of a closure cap of the present invention including an impervious elastomeric membrane covering used with a blood collection tube.

FIG. 3 shows one embodiment of the present invention. An improved closure cap in the form of cap 90 for blood collection tube 10 either is formed with, or matingly adapts to, membrane 20. Cap 90 is formed of a resiliently deformable material such as rubber, TPE, thermoplastic, plastic foam, or the like. Cap 90 includes an outer component in the form of a flat annular member 95 having opposed major surfaces 96 and 97, and an interior expanse 29 communicating through the two major surfaces. Major surface 97 includes a depending interior annular member 65 which is coaxial with interior expanse 29 for engagement with member 20. Cap 90 further includes a circumferential depending member 93 coaxial with interior expanse 29 and depending from the outermost portion of annular member 95. Member 93 preferably includes a depending annular skirt 98 flaring circumferentially outward to provide for frictional engagement with the interior wall 37 of holding device 30.

Cap 90 includes, or is attachable to, an elastomeric membrane 20 which is puncturable by hollow needle 40, as shown in FIG. 2. Cap 90 is preferably bonded to membrane 20 by an annular adhesive bond C located on lower surface 51 of interior annular member 65. Membrane 20, which preferably includes elastomeric disk 21 and gas barrier layer 22 is circumferentially bonded to the open end of tube 10 by an adhesive bond B. Cap 90 provides annular frictional bond A, resulting from the inward deflection of depending annular skirt 98 by holding tube 35.

Figure 4:
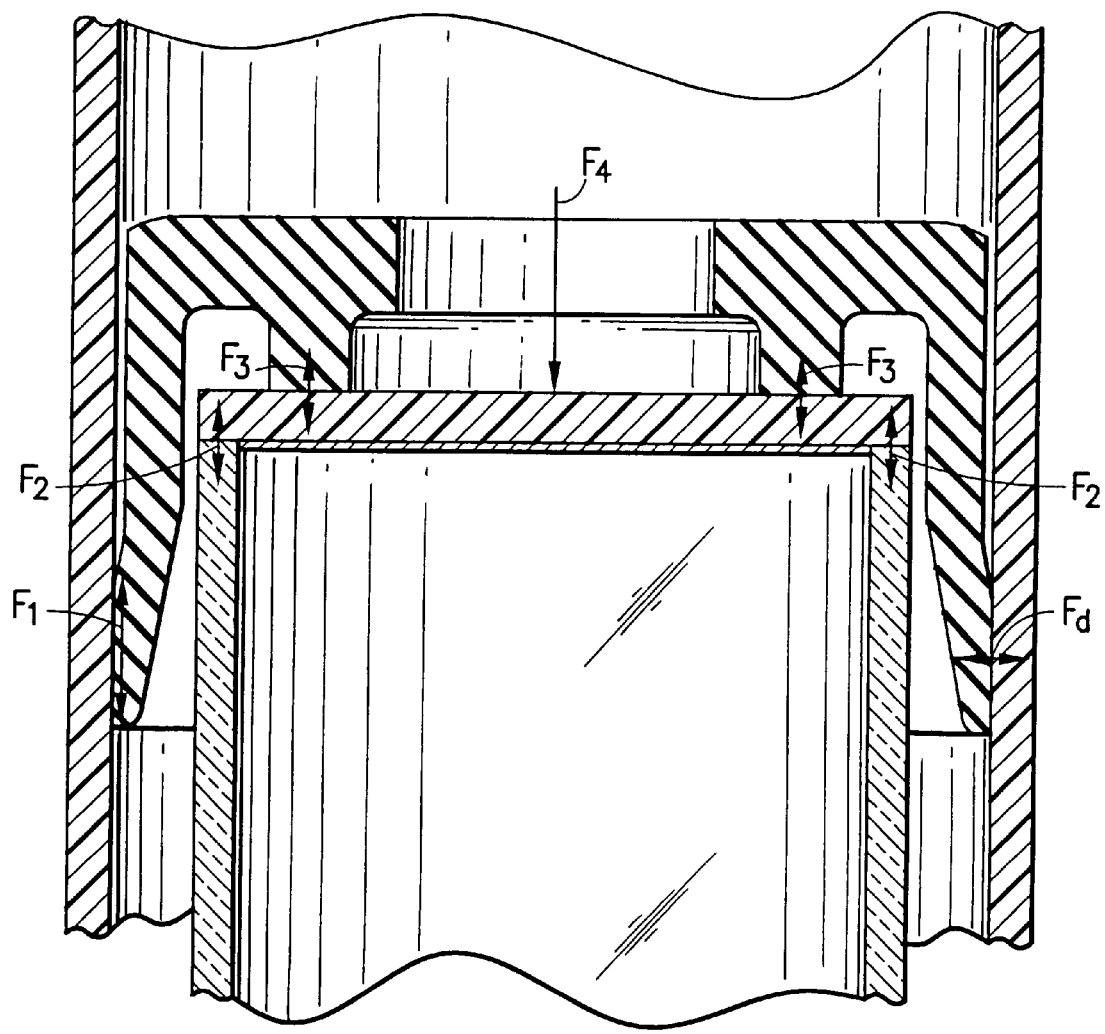
FIG. 4 shows a cross-sectional view of the blood collection tube and cap of the present invention positioned within a holding device.

FIG. 4 also shows the various engagement forces either provided by, or acting on, the present invention. $F_d$ is the radial deflection force exerted by holding tube 35 against depending annular skirt 98 of cap 90. Force $F_1$ is the frictional resistance force resulting from radial deflection force $F_d$ and which resists longitudinal movement of cap 90 within holding tube 35. Force $F_2$ is the bonding force holding membrane 20 to tube 10. Force $F_3$ is the bonding force holding the cap of the present invention to membrane 20. Force $F_4$ is the spring like sheath push-off force exerted by the compressed protective sheath 50 against the blood collection tube with the cap of the present invention. The relationship between frictional resistance force $F_1$, bonding forces $F_2$ and $F_3$, and sheath push off force $F_4$ is that force $F_3$ is stronger than force $F_2$ which is stronger than force $F_1$ which is stronger than force $F_4$. Alternatively stated, the relationship between the engagement forces is $F_3 > F_2 > F_1 > F_4$.

Figure 5:
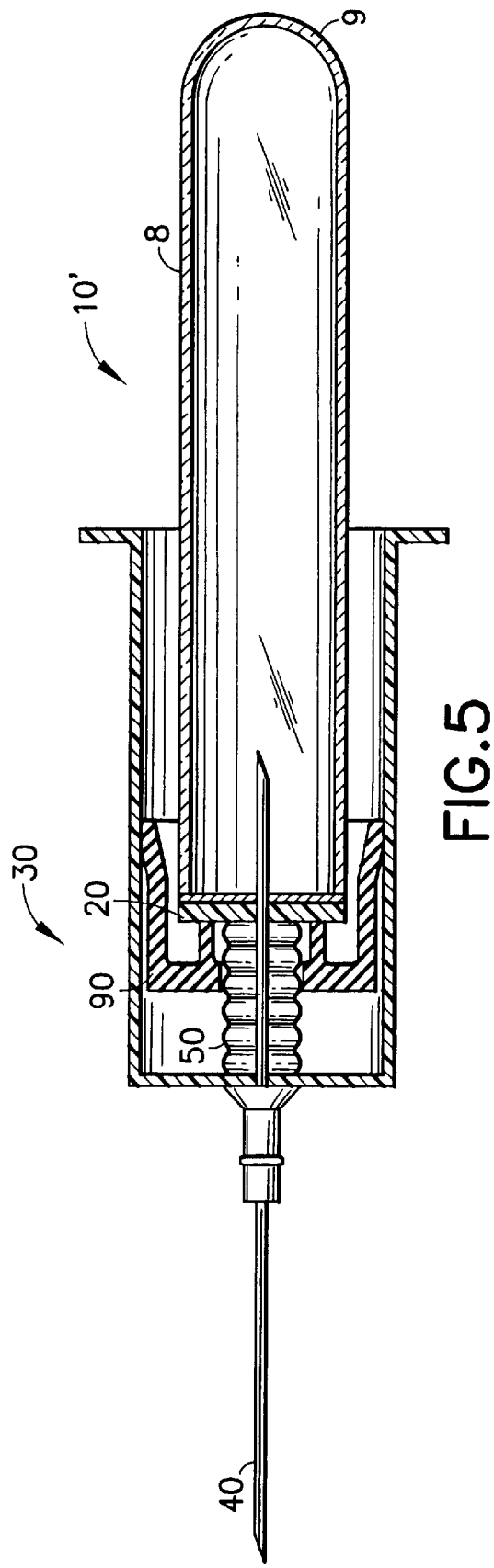
FIG. 5 shows a cross-sectional view of a combination of a blood collection tube with a closure cap of the present invention and a holding device having a needle with a protective sheath thereover.

In other words, and as shown in FIG. 5, when tube 10 with the cap assembly of the present invention is inserted into holding device 30 to draw blood, the frictional resistance force $F_1$ will overcome the spring-like sheath push-off force $F_4$ exerted by compressed sheath 50 against cap 90 and thereby maintain the blood collection tube 10 in the holding device 30. When tube 10 is then retracted from holding device 30 the force necessary to overcome frictional force $F_1$ will be less than either of bonding forces $F_2$ or $F_3$ so that the entire blood collection tube will pull out from the holding device 30 without coming apart at adhesive bonds B or C. Furthermore, should an operator desire to remove the cap assembly from tube 10, bonding force $F_2$ will be overcome first so that the cap assembly may be removed from the tube in one piece without separating cap 90 from disk 10. Such relationships between the engagement forces may also provide for the easy removal of disk 20 from tube.

The relationship between forces $F_1$ and $F_4$, as set forth in the present invention, provides a blood collection tube that can resist the expansion forces exerted by the compressed sheath of the holding device 30 so as to securely hold tube 10 within holding device 30 during the blood collection procedure.

Various other modifications to the foregoing disclosed embodiments will now be evident to those skilled in the art.

Thus, the particularly described preferred embodiments are intended to be illustrative and not limited thereto. The true scope of the invention is set forth in the following claims.

What is claimed is:

1. An assembly for the collection of a patient's blood specimen comprising:

an elongate blood collection needle having a blood extracting end and an opposed blood expelling end;

an elongate needle holder having an open end, an opposed closed end and a cylindrical wall therebetween defining a needle holder interior, said needle holder supporting said needle at said closed end with said blood extracting end extending exteriorly of said needle holder and said blood expelling end extending within said needle holder interior, an elongate blood collection tube having an open end, an opposed closed end and a cylindrical wall therebetween defining a tube interior, said blood collection tube being insertable into said needle holder interior for collecting blood from said expelling end of said needle through said open end; and a cap closing said open end, said cap having a membrane which is puncturable by said expelling end of said needle upon insertion of said blood collection tube into said interior of said needle holder, said cap including a deflectable member extending therefrom for engagement with cylindrical wall of said needle holder so as to provide a functional resistance force to frictionally resist longitudinal movement of said tube within said needle holder; wherein said cap includes a penetrable disk defining said membrane and an outer component securing said disk to said pen end of said tube, said deflectable member extending from said outer component and said outer component further comprising a depending interior annular member which is coaxial for engagement with said membrane and less in circumference than said membrane and thereby provides a bonding force F for holding said cap to said membrane and to prevent a peal type failure of said membrane.

* * * * *